US008753295B2

(12) United States Patent
Thierman (10) Patent No.: US 8,753,295 B2
(45) Date of Patent: Jun. 17, 2014

(54) TREATMENT OF WARTS AND OTHER DERMATOLOGICAL CONDITIONS USING TOPICAL ULTRASONIC APPLICATOR

(75) Inventor: Jonathan S. Thierman, Boston, MA (US)

(73) Assignee: Sure-Shot Medical Devices, Las Vegas, NV (US)

( * ) Notice: Subject to any disclaimer, the term of this patent is extended or adjusted under 35 U.S.C. 154(b) by 1122 days.

(21) Appl. No.: 11/652,910

(22) Filed: Jan. 11, 2007

(65) Prior Publication Data

US 2008/0027359 A1     Jan. 31, 2008

Related U.S. Application Data

(60) Provisional application No. 60/758,341, filed on Jan. 11, 2006.

(51) Int. Cl.
    *A61H 1/00*     (2006.01)
(52) U.S. Cl.
    USPC ........................................ 601/3; 601/2; 601/4
(58) Field of Classification Search
    USPC ................... 600/439, 549; 601/2–4; 604/22
    See application file for complete search history.

(56) References Cited

U.S. PATENT DOCUMENTS

| 5,421,816 | A | * | 6/1995 | Lipkovker | ...................... 604/20 |
| 5,618,275 | A | | 4/1997 | Bock | |
| 6,183,426 | B1 | | 2/2001 | Akisada et al. | |
| 6,325,769 | B1 | | 12/2001 | Klopotek | |
| 6,500,133 | B2 | * | 12/2002 | Martin et al. | ..................... 601/3 |
| 6,569,170 | B1 | * | 5/2003 | Kellogg | ........................ 606/131 |
| 6,595,934 | B1 | | 7/2003 | Hissong et al. | |
| 6,821,274 | B2 | * | 11/2004 | McHale et al. | ................. 606/41 |
| 2005/0049543 | A1 | | 3/2005 | Anderson et al. | |
| 2005/0251117 | A1 | | 11/2005 | Anderson et al. | |
| 2007/0078290 | A1 | | 4/2007 | Esenaliev | |
| 2007/0135876 | A1 | | 6/2007 | Weber | |

FOREIGN PATENT DOCUMENTS

| WO | WO 98/32379 A1 | 7/1998 |
| WO | 00/21612 A1 | 4/2000 |
| WO | 02/09813 A1 | 2/2002 |

* cited by examiner

*Primary Examiner* — Tse Chen
*Assistant Examiner* — Mark Remaly
(74) *Attorney, Agent, or Firm* — Intrinsic Law Corp.; Ibrahim M. Hallaj (57) ABSTRACT

A method and system including an applicator for treating dermatological conditions such as warts is presented for applying ultrasonic energy from a specially-designed ultrasonic energy applicator designed for use with localized dermatological conditions to heat an affected localized region sufficiently to achieve a desired therapeutic result. Specific embodiments include temperature measurement and/or sensing and/or actuation by way of a temperature sensor coupled to the ultrasonic energy applicator. Also, a medicated ultrasound-compatible patch is disclosed for applying to a region of tissue to be treated and includes substances known to aid in the treatment of a condition and adapted for transmitting the ultrasound energy into the region of tissue.

17 Claims, 8 Drawing Sheets

Fig. 8

TREATMENT OF WARTS AND OTHER DERMATOLOGICAL CONDITIONS USING TOPICAL ULTRASONIC APPLICATOR

This application claims benefit of priority to U.S. Provisional Application No. 60/758,341, filed on Jan. 11, 2006, the entire content of which is incorporated by reference herein.

TECHNICAL FIELD

The present disclosure relates generally to the field of dermatological treatment of skin conditions such as warts and other conditions near the surface of the skin. Specifically, systems and methods for treating such conditions using an ultrasonic applicator are disclosed and claimed.

BACKGROUND

Certain conditions existing at or near the surface of the skin, e.g. as caused by the Human Papilloma Virus (HPV) which causes plantar (*Varuca Plantaris*), genital (*Condyloma Acuminata*), and other types of warts, can be treated by elevating the temperature of the affected region. Ultrasonic energy deposition is known to elevate temperature in tissue. It is known that elevating the temperature at an affected region will cause physiological and/or medically significant mechanical biological change such as death of the organisms responsible for the condition. Traditional treatments include large volume heating such as using hot water baths of an appendage, e.g., hand, foot, finger, etc. to achieve the temperature elevation required for treatment. However, such traditional treatments are awkward and painful to the patient, and expose healthy regions of the treated organ to temperature elevations which are not required on the whole organ or which could be harmful to the whole organ.

SUMMARY

Embodiments of the present disclosure are directed to an ultrasonic device for thermal treatment of medical conditions near a skin surface, comprising an ultrasonic source adapted for depositing acoustical energy into a region of tissue near the skin surface; a housing that houses the ultrasonic source and houses a supply of power to the ultrasonic source; wherein said ultrasonic applicator is of a size and form to be manually held and applied to said region of tissue; and wherein said housing includes the ultrasonic source and supply of power to the ultrasonic source.

Other embodiments are directed to a method for treatment of a medical condition near a skin surface, comprising applying a medicated patch onto a region of tissue being treated, said medicated patch including a substance known to favorably affect treatment of the medical condition being treated; applying to the medicated patch an ultrasonic source adapted for depositing acoustical energy into a region of tissue near the skin surface; manually manipulating said ultrasonic source by holding the source so as to deposit energy from the ultrasonic source into the region of tissue being treated through said medicated patch; and determining when a sufficient thermal effect of the deposited energy into the region of tissue being treated has been obtained to secure the treatment.

Yet other embodiments are directed to a medicated patch for treatment of a skin condition, comprising an adhesive band adapted for adhering to a region of tissue being treated; said adhesive band including a first surface having an adhesive material for adhering to the skin around said region of tissue being treated; said adhesive band further including a second surface adapted for coupling to an ultrasonic source for treating said region of tissue; said patch being designed and adapted to pass ultrasonic waves from said ultrasonic source into said region of tissue; and said patch including medication known to aid the treatment of said skin condition.

Still other embodiments are directed to an apparatus for treating a skin condition, comprising an ultrasonic source designed to provide energy to a region being treated and elevating the temperature of the same; a self-contained source of power for driving said ultrasonic source that is not connected to an external power source during operation of the apparatus; a control circuit for controlling the driving of said ultrasonic source; a temperature sensor that senses a temperature of said region being treated and provides a signal to said control circuit; and a housing that houses at least said ultrasonic source, said self-contained source of power, said control circuit, said housing being sized and formed to provide portable hand-held operation of the apparatus for localized treatment of said skin condition.

DETAILED DESCRIPTION

The present disclosure is generally directed to methods for treating localized dermatological conditions in humans and other animals using ultrasound applied to affected dermal tissue (skin) regions to raise the temperature of the affected region at the affected location to a desired level or threshold. The conditions known to respond to heat treatment include Human Papilloma Virus (HPV) which causes plantar warts (*Varuca Plantaris*) and genital warts (*Condyloma Acuminata*) as well as other types of warts. Also, it has been proposed that acne may respond to heat treatment either by direct denaturing of the common bacteria contributing to acne such as Proprionibacterium acnes among other or by affecting local perfusion to the area of skin or by affecting the production or consistency of the sebum and free fatty acids that are formed and contribute to acne production. The accumulated thermal dose may be considered in the treatment of the affected regions, depending on the specific application at hand. Generally, a source of ultrasonic acoustic energy is used to deposit energy onto, into, at, or around the affected region to raise its temperature. After the temperature of the target region reaches the desired level, optionally monitored or controlled by a sensor and/or actuator, the thermal treatment of the affected region can be stopped or otherwise proceed.

In practice, the ultrasound applicator is relatively compact and low-powered for the types of applications, e.g. treatment of warts, such as to raise the target volume temperature to about 113 degrees Fahrenheit (or 45 degrees Celsius). Other peak or threshold or average temperatures are contemplated for achieving this result, depending on the specific condition being treated and the condition of the patient.

The applicator may be compact and light-weight enough to be hand-held by a practitioner or the patient himself and may be portable and even battery powered. While the ultrasonic applicator may be powered by alternating current (AC) power, it is sometimes useful to have a portable device that can be powered by direct current (DC) power, for example an internal disposable or rechargeable battery or modular battery pack such as is used in portable power tools and personal appliances. Specific examples include the ability to power the device or recharge the device's battery packs from a wall outlet, e.g., a 120 VAC 60 Hz power source or a 210 VAC 50 Hz power source, as well as conversion from AC to DC power within the device itself or by using an auxiliary power pack disposed inline with the AC power cable for the device.

The packaging or housing in which the ultrasonic applicator is provided can take any of numerous shapes, forms and sizes. For example, if the device is to be hand-held it may be useful to shape and form the device so that it can be easily gripped by the person using the device. Therefore, shapes and forms that are variations of cylindrical with contours accommodating the human hand are examples of packaging or housing of such a device so that it may be effectively and conveniently used in a clinical setting or in an outpatient facility or for home use. Helpful manufacturing techniques and coatings, such as comfort grips or polymer or rubber non-slip coatings may be applied to the exterior surface of the hand-held device to make it easier to hold and use. In some embodiments, it is envisioned that a device being self contained and compact enough to fit in a pocket or small tool case can be provided. The device may have a pen-like form factor or a wand-style form factor suitable for hand-held applications for treating topical conditions like warts. The device may have a "tip" at one end of its elongated body that is used to treat the condition, and is sized to fit over the entire affected region or portions thereof.

Figure 1:
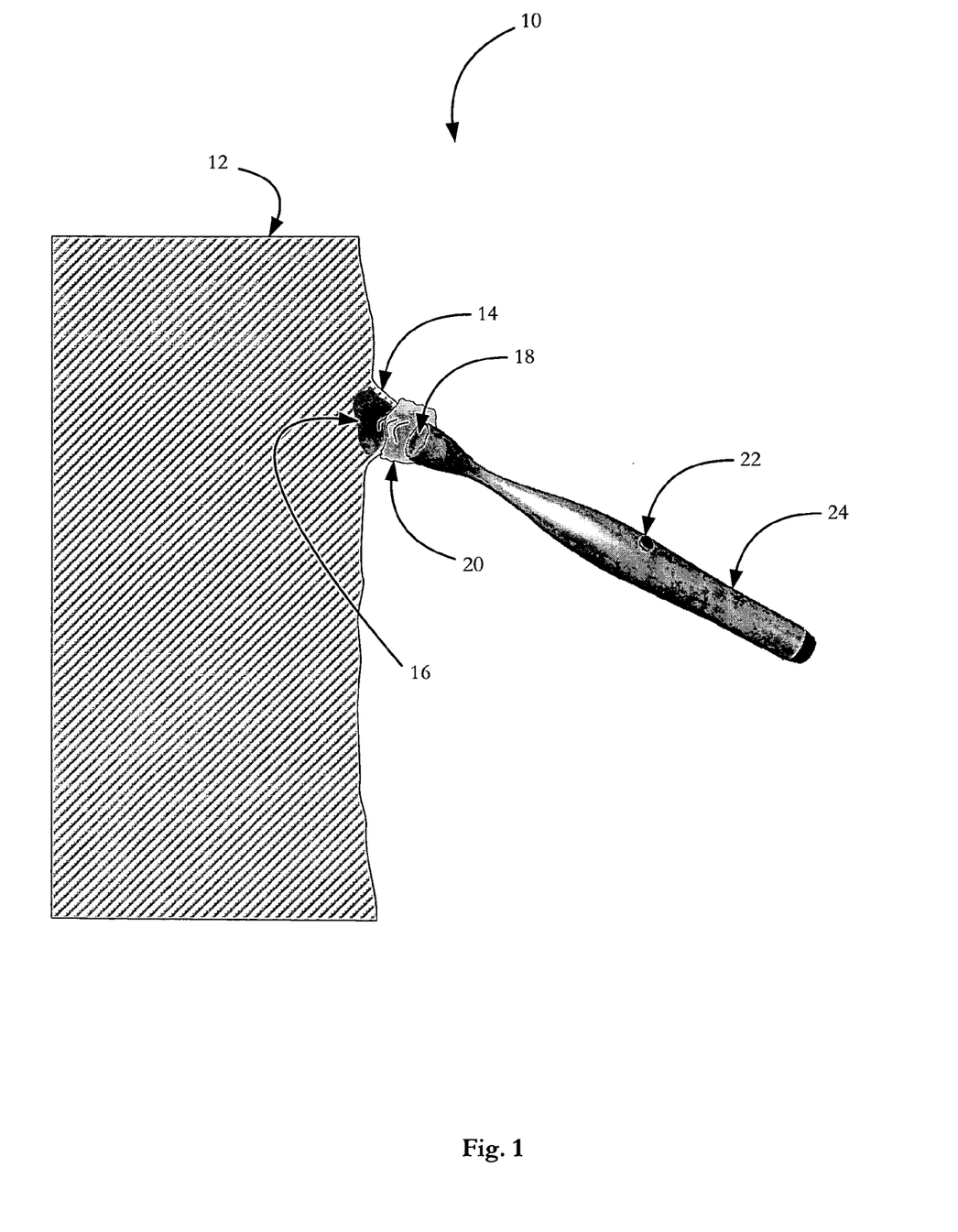
FIG. 1 illustrates a view of a hand-held ultrasonic applicator device being applied to the surface of a region of tissue being treated.

FIG. 1 illustrates a representation of the present apparatus 10 in use to treat a lesion 14 at or near the surface of the skin 12 of a patient. A lesion (e.g., a wart) 14 to be treated is substantially at the surface of the patient's skin 12 and typically includes bacteria or virus (e.g., HPV) intended to be treated with the applicator apparatus. The lesion 12 is heated by energy provided from an ultrasonic source (e.g., transducer) 18. The transducer 18 may be itself focused or may be unfocused but provided with a focusing element to direct the acoustic energy onto a region 16 near the surface of the skin at the region being treated, ideally confining the energy and resultant heating to the region 16 of the lesion.

To provide a better ultrasonic coupling for the acoustic energy from the transducer 18 to the affected region 16, a coupling gel 20 is applied to the area around the lesion 14. The coupling gel 20 may include medication to enhance the treatment, be of an acoustical or other nature to promote the transmission of acoustic ultrasonic energy effectively and efficiently into the treated region, and may be in a medicated pad form factor applied to the skin. The pad may adhere on one side to the skin for more convenient application.

A power switch (ON/OFF) 22 is provided at a location on the device 10 so that the user can actuate the power to the transducer by clicking, switching, turning, depressing, or otherwise operating the switch 22. The switch 22 may be replaced with or include a variable power element to turn the power applied to the transducer 18 up or down in gradual (continuously variable) or in stepped increments. A dial or sliding element can be used to control the output power of the transducer 18.

The device 10 is included within a housing or body 24 that houses the elements described above. The housing 24 may also include a cavity for the power supply to the portable device. For example, a cavity in the housing 24 can contain one or more disposable, rechargeable, or other battery elements. The housing 24 can also contain a power supply that can be disconnected from an external source of power, e.g., a power pack that can be charged from an AC source, but then disconnected for portability during use.

Optional user interface elements may also be provided on the device, such as a timer that indicates a time elapsed or time remaining for a treatment. An indication of lesion temperature, thermal dose, or other parameters meaningful to the treatment of the condition can also be displayed.

The device can be further equipped with a pen-like clip that keeps the device securely in a pocket. The device can also be equipped with a belt clip or loop so that it is securely kept on the practitioner's belt and readily accessible. Also, a protective case can be used around the device to protect it from becoming dirty and from damage if dropped. The protective case may itself be equipped with the pen-style holding clips or belt clips or loops. The protective case may be padded. The protective case may also include openings or apertures for treating through the protective case or a flip-top portion that allows for treatment without removing the device from the case. The protective case may also include openings through which power connections may be made for powering or recharging the device.

To generate the therapeutic acoustical output, the ultrasound applicator device generally includes an ultrasonic energy source, e.g. an ultrasonic transducer 18, which converts electrical energy to ultrasonic acoustic energy. Common examples of such a transducer are piezo-electric transducer sources (PZT) that includes a PZT crystal which vibrates at a design frequency and power upon application of electrical power to terminals of the PZT crystal. The resulting vibration of the source emits acoustic waves or energy which can be designed to travel out of the device, sometimes through a variety of coupling media, to effectively reach its intended target.

One example is a focused source 18 where the PZT crystal itself can be shaped to deliver acoustic waves that intensify or "focus" by geometric superposition at a focal spot or region. The focal spot or region can be generally designed and controlled depending on the desired use of the device as known to designers of ultrasonic sources.

Another focused source 18 can be constructed by placing an unfocused (usually flat) PZT crystal in a housing that acts to redirect the acoustic energy of the crystal onto a focal region or spot by reflecting or refracting of the acoustic waves towards the focal spot or region. Focused sources are characterized by an elevated acoustic intensity, energy, or pressure amplitude at or near the focal region. This in turn can be used to control and constrain the major heating effect of the source 18 to a region 16 at or near the focal region of the source, thereby avoiding undesired heating or damage to surrounding tissue 12. In the case of wart or topical dermatological treatments, this can be used to spatially limit the thermal therapeutic treatment to the affected region 16.

To achieve an effective spatially-localized treatment and deliver the ultrasonic energy from the source to the affected treatment volume, a coupling medium 20 can be used. The coupling medium 20 is typically a disposable liquid or gel, such as is sold commercially (e.g. Aquasonic® gel) that replaces the air between the ultrasonic source and the desired treatment area and acts as a waveguide that carries the acoustic energy from the ultrasonic source 18 to the patient's body. The coupling material or gel 20 may be wiped clean from the applicator 10 and the patient's body after the treatment is complete. Also, disposable membranes or convenient plastic tip covers can be used to maintain the hygienic environment of clinical or home use. Such membranes or plastic tip covers are generally transparent to the acoustic waves and do not significantly affect the effectiveness of the ultrasonic applicator device 10.

In some embodiments, an adhesive patch is applied to the region of tissue being treated. The adhesive patch includes a band that has adhesive on one side so as to stick to the skin around the region being treated. The other side of the band does not include adhesive, but is adapted to couple with the source of ultrasound to transmit energy from the ultrasonic source into the region of tissue being treated. The adhesive patch can be medicated on the side facing the patient's skin. The medication is a substance, such as salicylic acid or including an acid as an ingredient, that is known to aid in the treatment of the condition. Salicylic acid is one example that is believed or known to aid in the treatment of skin warts. Therefore, the ultrasonic device can enhance the delivery of the medicated substance onto and/or into the region being treated. Furthermore, the medicated substance's effect is coupled with the heating effect of the deposited ultrasonic energy in, on, or near the region of tissue being treated. So in some specific examples, salicylic acid from the medicated patch is applied to the exterior surface of the region being treated while the ultrasonic energy heats the region, including some small depth below the surface of the skin to a temperature of about 113 Fahrenheit.

The temperature is monitored, and in some embodiments is used to control the application of ultrasonic energy to avoid excessive heating or damage to tissue outside the region being treated and to avoid undue pain to the patient.

Ultrasonic coupling media can be used in some embodiments to enhance the delivery of ultrasonic waves and energy to the region of tissue being treated. This includes by designing and adapting the adhesive medicated patch to efficiently pass ultrasonic waves and energy from the ultrasonic source into the region of tissue being treated. That is, to minimize the loss of acoustical energy as the ultrasonic waves are incident upon the medicated patch and passing through it. In some cases, a special fluid coupling medium, such as a gel, can include a medicated substance such as salicylic acid, that enhances the treatment of the skin condition. So, adding salicylic acid or other suitable medicinal substance to an acoustic gel compound or coupling medium can be done to enhance the effectiveness of the treatment.

Temperature sensing and control can be affected in any of a number of suitable ways. In some embodiments, a temperature sensor is placed in, on, or around the ultrasonic source transducer. For example, an opening can be cut within the face of the transducer and a temperature sensor that relies on electrical signal feedback or an infrared sensor can be placed within the opening. Such an aperture for the temperature sensor can be disposed substantially near the center of the ultrasonic transducer.

In other embodiments, a specially-made ultrasonic coupling pad can be designed to pass the ultrasonic waves and energy from the ultrasound source and the pad can include a temperature sensing probe within it and near enough to the surface of the region being treated such that the probe can provide an indication of the region of tissue being treated. The specially-made coupling pad is therefore designed to be electrically coupled to a matching connector on the treatment device so that the temperature signal can be passed from the sensing probe in the pad to the circuitry within the treatment device. Such coupling pads can be re-usable or disposable. In the case of disposable coupling pads with temperature sensors therein, the pad/sensor element should preferably be made inexpensively and come in dispensers that are convenient for practitioners to pull out successive disposable pads for use.

Signals generated responsive to the measurements of temperature on, at, or in the region of interest can be used by electronic or microprocessor circuits within the hand-held apparatus so that the temperature of the region of tissue being treated can be determined and used to control the application of the treatment or securing the treatment. Securing the treatment can be triggered by a temperature at or around 113 Fahrenheit. The ultrasound device can also compute, estimate, or rely on a measure of thermal dose to do the same.

Figure 2:
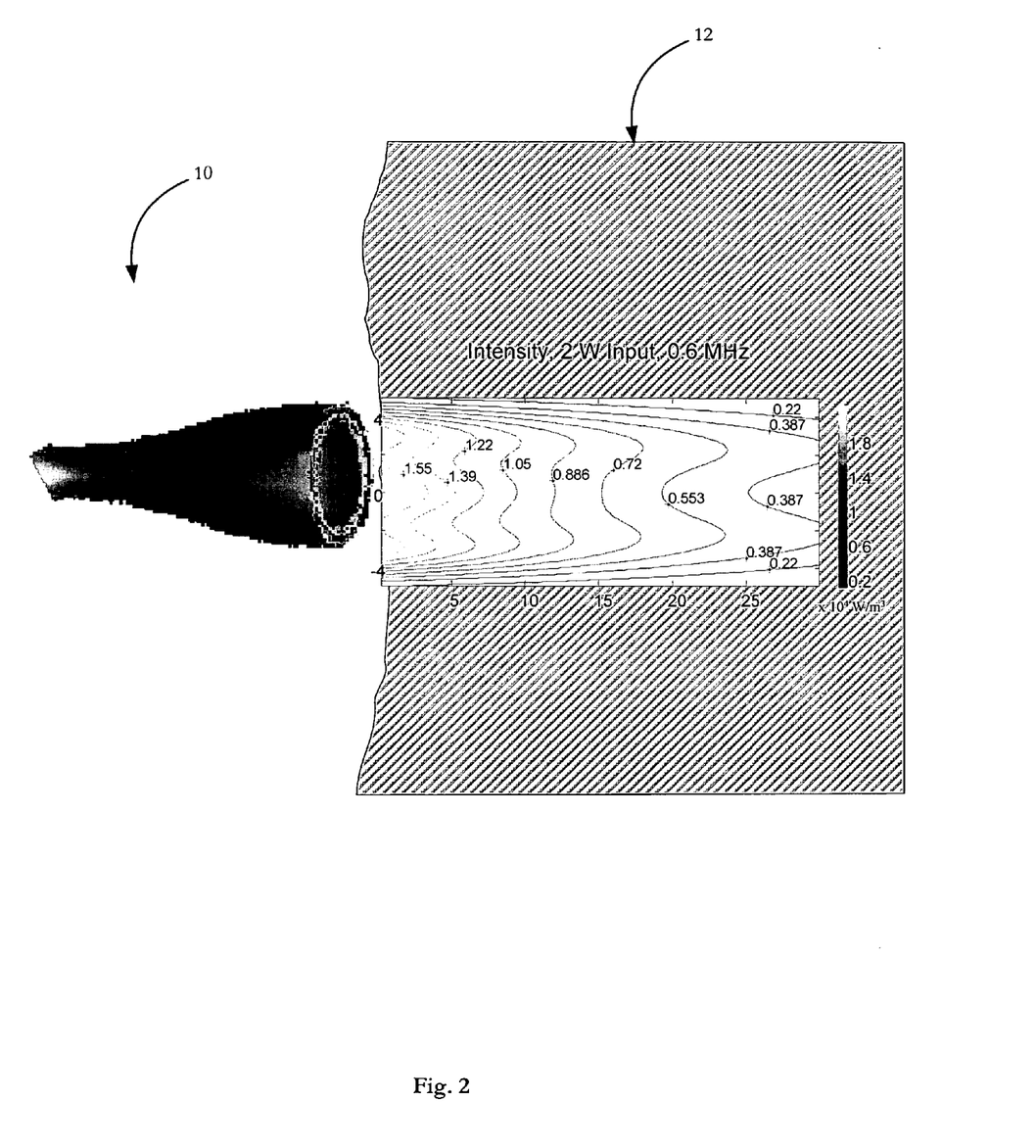
FIG. 2 illustrates a generalized concept of localized heating from application of ultrasonic energy to a region of tissue being treated, with the acoustical intensity field in and around the region of tissue (the dermis and epidermis) being depicted.

FIG. 2 illustrates an exemplary configuration of a portable treatment device 10 being applied to the skin 12 of a patient and treating shallow regions of the patient near the skin's surface. Note that the heating is localized to the region near the surface of the skin and near the face of the transducer. The device described herein is optimally suited for treatment of shallow regions of tissue (e.g., those at the surface of the skin or at depths less than about 25 mm beneath the surface of the skin). That being, the present device is generally not designed to reach and treat deep regions of tissue (e.g., at a depth greater than 25 mm beneath the surface of the skin). In some embodiments, the conditions best treated with the present device are those such as warts that are on or at or substantially near the surface of the skin. In some specific instances, the treated regions may even protrude above the surface of the skin slightly. In other specific instances, the treated regions would be substantially flush with the surface of the skin 12. In some specific instances, the region being treated extends a few (e.g. five or less) millimeters beneath the surface of the skin. No appreciable deposition of ultrasonic energy or attendant heating is expected much deeper than the depth of the region of tissue being treated. In fact, in some aspects, one advantage of the present device is the localization of its energy and heat deposition to the affected regions of tissue to substantially only treat the affected regions and their immediate surrounds. Those skilled in the art will appreciate however that with any radiating or wave propagating source directed at the surface of the skin that sends acoustic waves into the tissue, that some finite although small amount of acoustic energy will propagate and might be measurable deep into the tissue.

Figure 3:
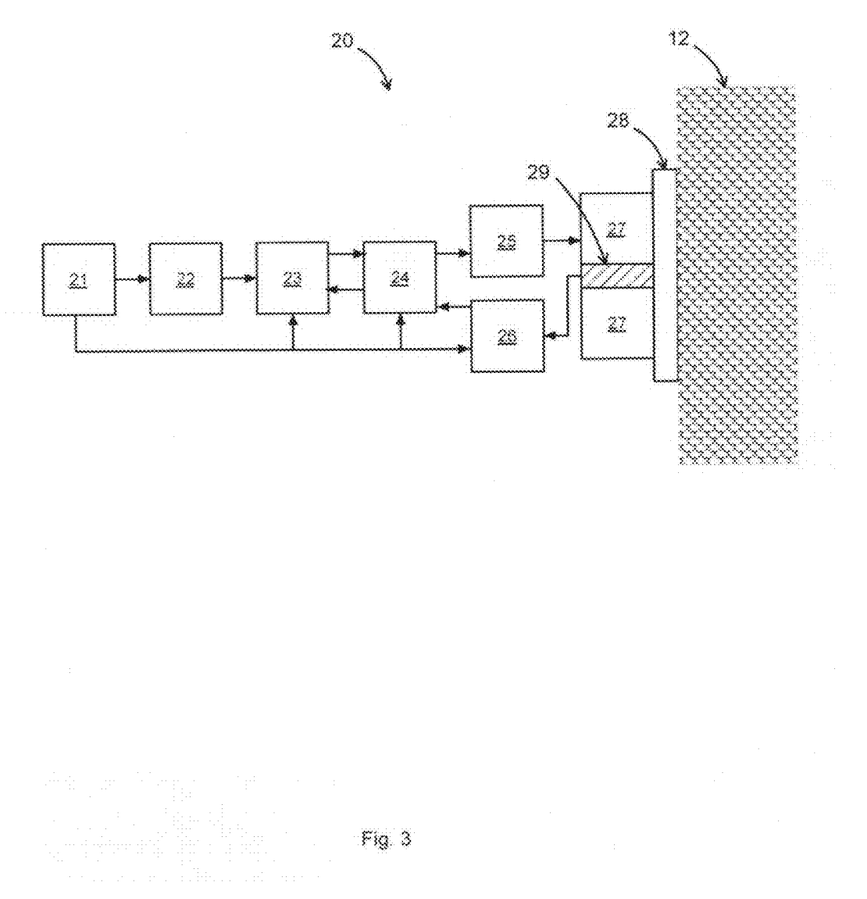
FIG. 3 illustrates a schematic diagram of the circuitry for supplying power to the ultrasound transducer and sensing the temperature of the surface of the skin at the region being treated.

FIG. 3 illustrates a schematic diagram of an exemplary system and associated circuitry 20 for powering and controlling the treatment according to one or more embodiments of the present invention. Various components shown can be replaced or removed in some embodiments without defeating the overall purpose of the system. Also, some components are not shown or are shown in a block diagram where they could be replaced by more than one sub-component. Also, the components shown can be rearranged and the ordering and interconnection between the components is not necessarily required for each embodiment of the invention.

Transducer 27 is powered to provide heating through coupling medium 28, which may be a gel pad, including embodiments of a medicated gel pad, to an affected region of tissue near the skin surface, such as a lesion or a wart. Generally, the system 20 includes a power supply 21 as described above, which in some embodiments includes a disposable or rechargeable battery. The power supply 21 may be actuated with a power switch or a power control device as discussed previously. The system includes a frequency generator 22, which in some embodiments provides a constant frequency signal such as a sinusoid or a square wave or another substantially periodic signal. The signal from frequency generator 22 is amplified with a radio frequency (RF) amplifier 23 to increase its amplitude to drive the other components of the system. Control circuitry 24 can be used to control the other components of the system, and various features to be controlled have been described above and would be known to those skilled in the art upon review of the present disclosure. The control circuitry 24 may include one or more solid state components or groups of components, processors, memory storage locations, communication buses, and other devices to perform its function. The system also includes a matching circuit 25.

In addition to driving transducer 27 to affect the heating treatment, the system includes a temperature sensor 29 that senses a temperature of the treatment volume or another region associated with the thermal treatment taking place. In the present embodiment, which is not provided by way of limitation, the temperature sensor 29 is disposed within a cavity in the transducer 27. For example, transducer 27 may be provided with a cut-out near its center within which temperature sensor 29 is placed. Sensor circuitry 26 receives an input from temperature sensor 29 and provides a corresponding output to control circuitry 24. In this way, a temperature or thermal parameter such as the integrated thermal dose can be calculated and the treatment controlled accordingly.

Figure 4:
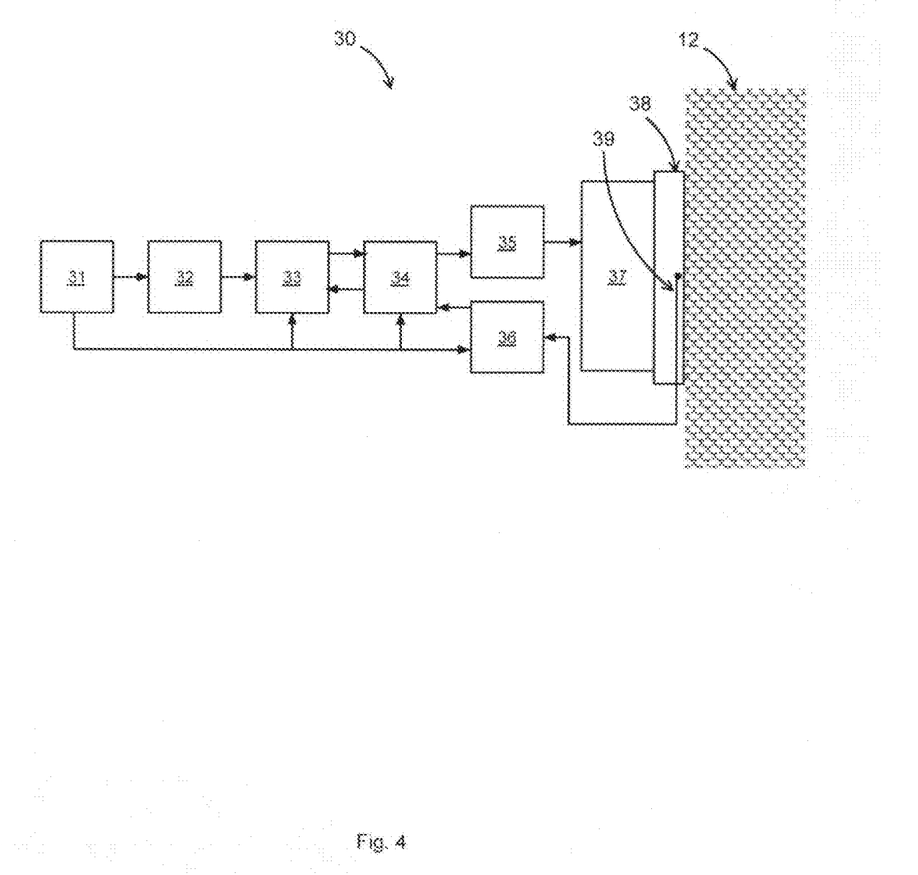
FIG. 4 illustrates another schematic diagram of a system for treating skin and surface tissue conditions with a temperature sensor inside a coupling pad.

FIG. 4 illustrates another exemplary system 30 for treating a skin condition or lesion near the surface of the skin 12. In this embodiment, temperature sensor 39 is disposed within special coupling medium 38, which may be a gel pad or even a medicated gel pad. An electrical connection is provided so that the temperature sensor 39 can communicate an electrical signal to the sensor circuitry 36. Other components of the system 30 are the same or similar to those described with respect to FIG. 3, or can be modified to accommodate the differences required by the alternate design of the temperature sensor 39. For example, system 30 may in one embodiment still utilize a power supply 31, a frequency generator 32, a RF amplifier 33, a control circuit 34, a matching circuit 35, and a sensor circuit 36.

Figure 5:
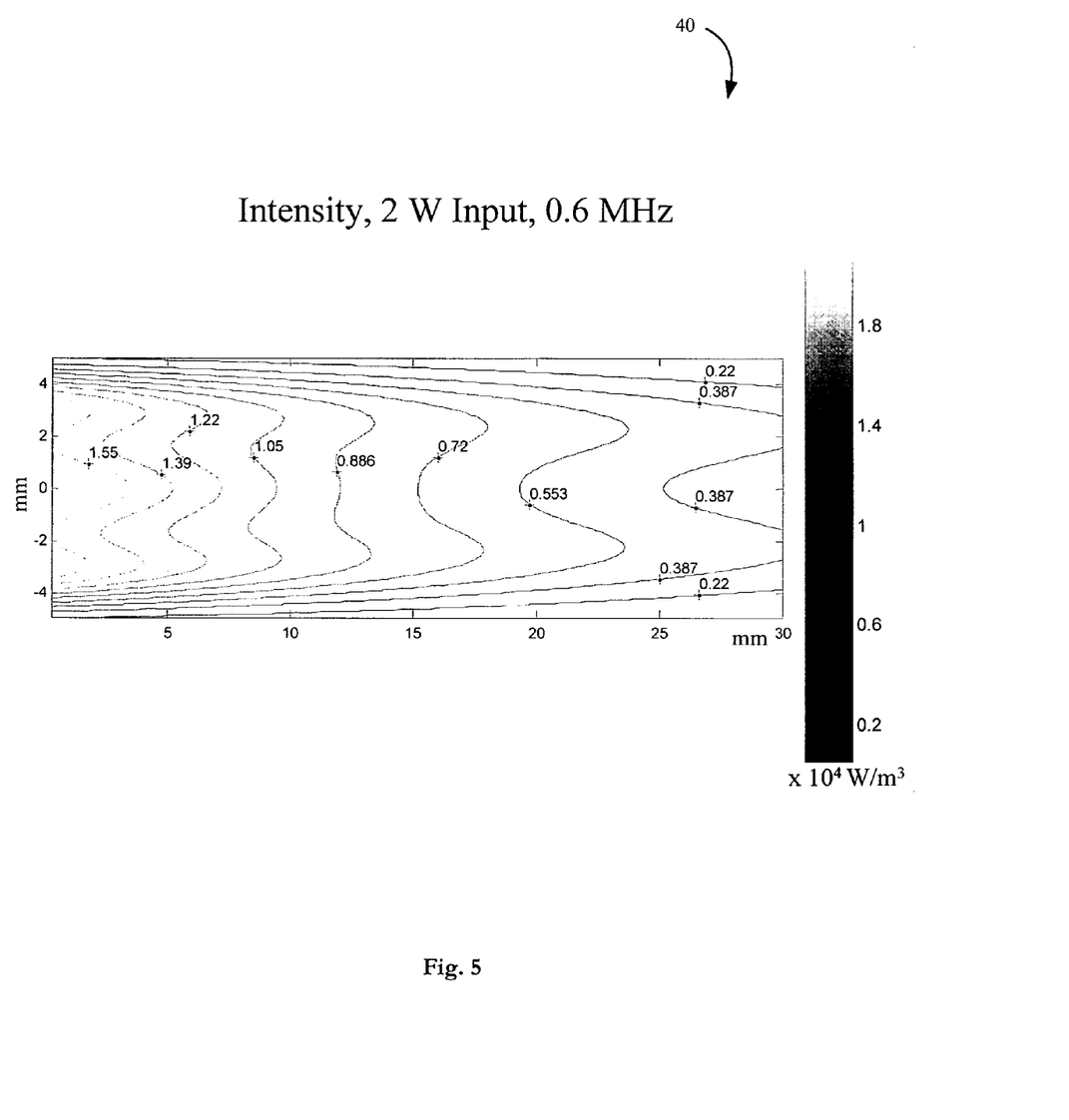
FIG. 5 illustrates an exemplary intensity plot showing how the ultrasonic field is focused at depths below the surface of the skin for a 2 W power transducer operating at 0.6 MHz and having a 10 mm diameter aperture applied at the surface of the skin.

FIG. 5 illustrates an exemplary intensity plot 40 showing how the ultrasonic field is focused at depths below the surface of the skin under certain design conditions for a 2 W power transducer operating at 0.6 MHz and having a 10 mm diameter aperture applied at the surface of the skin. Those skilled in the art would appreciate that this intensity profile would generate a heating effect.

Figure 6:
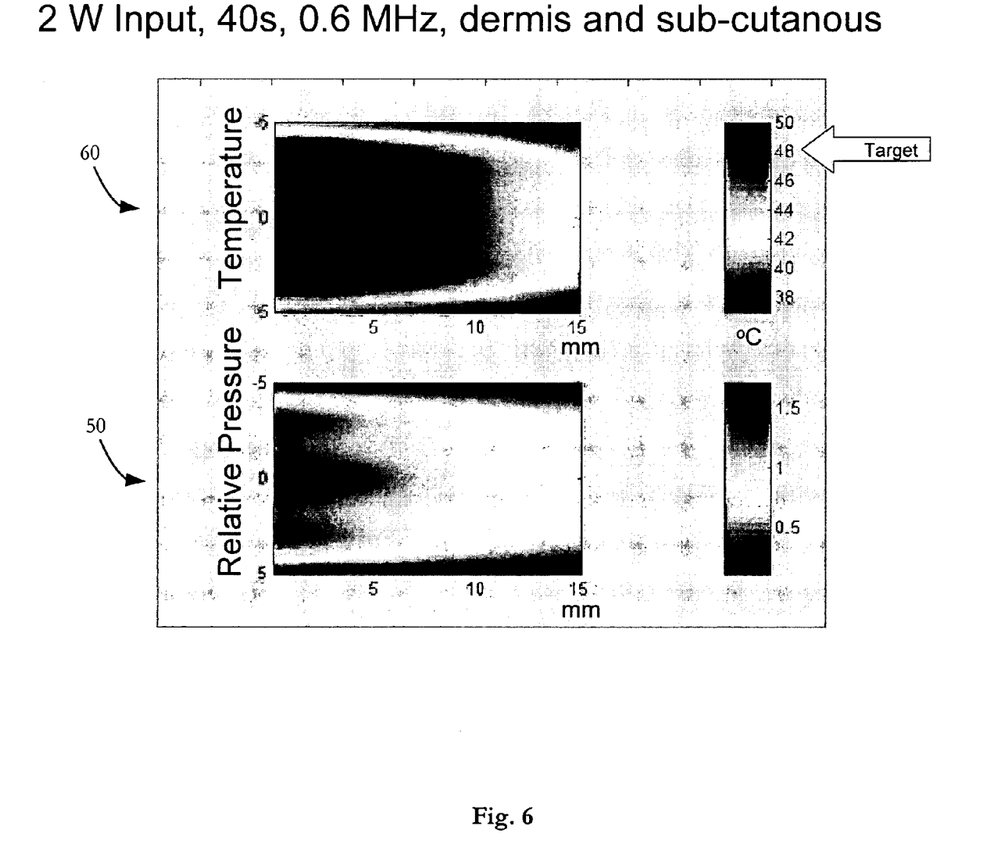
FIG. 6 illustrates an exemplary relative acoustic pressure and corresponding heating (temperature) profile resulting from a 40 second sonication.

FIG. 6 illustrates an exemplary relative acoustic pressure 50 and corresponding heating (temperature) 60 profile resulting from a 40-second sonication with the device described above in ordinary tissue. Note that a heated region results at a depth of about 12 mm below the surface of the skin.

Figure 7:
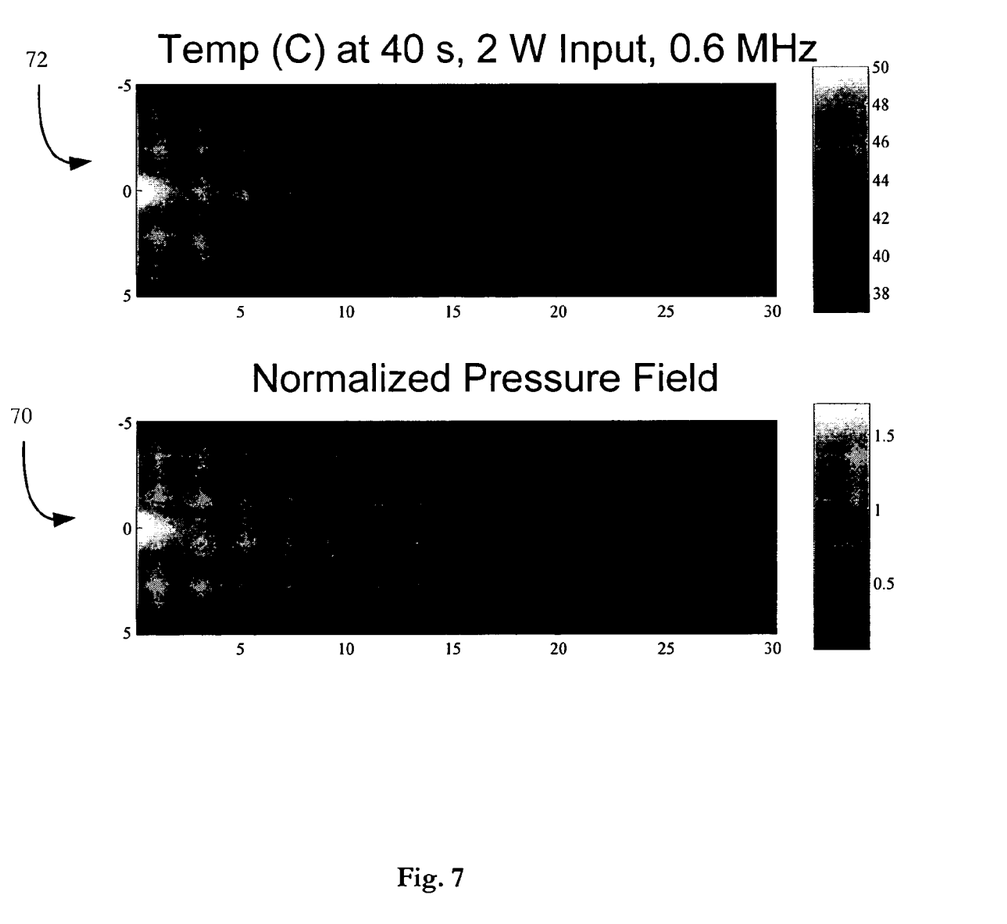
FIG. 7 illustrates exemplary pressure and temperature fields resulting from the application of a 20-second sonication to an affected region of tissue.

FIG. 7 illustrates exemplary pressure 70 and temperature 72 fields resulting from the application of a 20-second sonication using the device described above.

Figure 8:
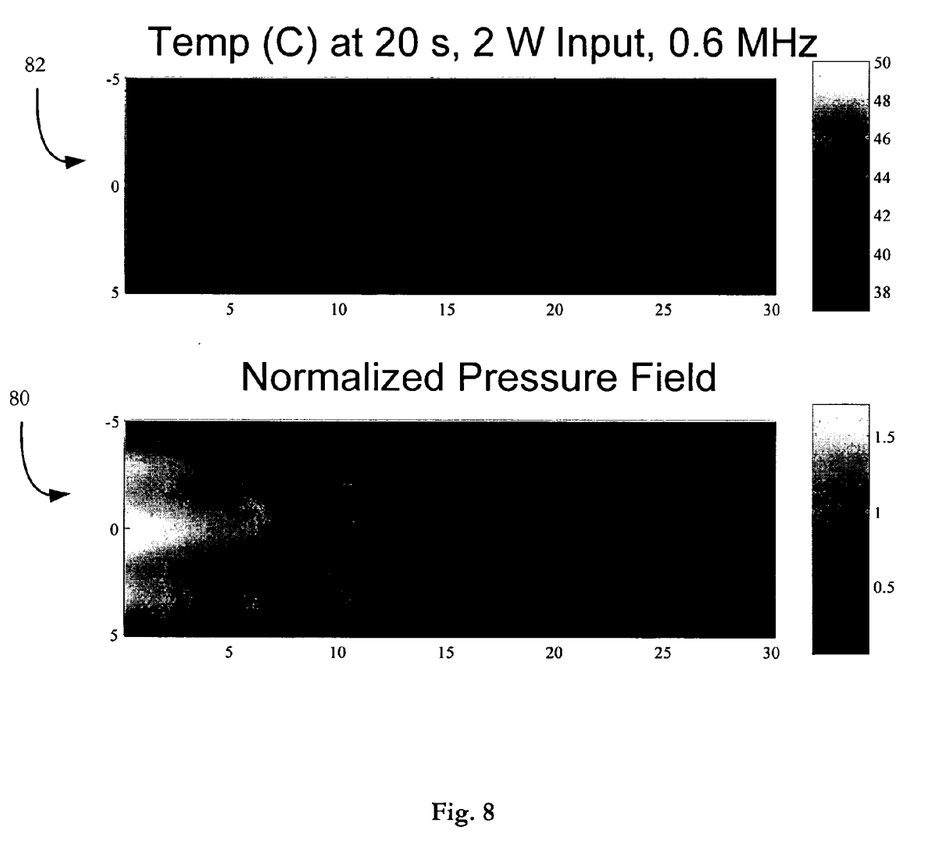
FIG. 8 illustrates exemplary pressure and temperature fields resulting from the application of a 40-second sonication to an affected region of tissue.

FIG. 8 illustrates exemplary pressure 80 and temperature 82 fields resulting from the application of a 40-second sonication using the device described above. Comparing FIGS. 7 and 8, it can be confirmed that the longer sonication results in larger temperature rises because of the larger integrated thermal dose applied to the affected region being treated. The device is in some embodiments designed to limit or control the temperature rise at the treatment location according to a clinically determined need.

It should be apparent to those skilled in the art that the present disclosure enables and teaches other specific embodiments and modifications and adaptations of the same that lie within the same scope and that are delimited by the claims below.

What is claimed is:

1. A compact portable ultrasonic device for thermal treatment of medical conditions near a skin surface, comprising:
    a focused ultrasonic source, having a diameter not exceeding 10 millimeters and a focal depth not exceeding 25 millimeters, configured and dimensioned to deposit acoustical energy into a target region substantially limited to tissue near the skin surface and proximal to a skin dermatological condition site so as to treat said dermatological condition at said site of the skin through thermal action;
    a narrow, elongated and compact housing that houses the ultrasonic source proximal to a first end thereof and houses a supply of power to the ultrasonic source;
    said housing being further configured to be hand-held and contoured to accommodate the human hand, and being configured in an overall form factor so as to allow manipulation of said first end to be applied substantially over an area limited to said target region;
    a temperature sensor that provides an indication of temperature in said target region; and
    a power control circuit, receiving an input from said temperature sensor, configured to cause activation of said ultrasonic source so as to achieve a temperature of approximately 113 F in said target region.

2. The device of claim 1, wherein the supply of power is adapted to be independent from external sources of power during use.

3. The device of claim 1, wherein the ultrasonic source has a focal depth substantially less than 5 millimeters beneath the skin surface and a radius of treatment substantially less than 10 millimeters.

4. The device of claim 1, wherein the ultrasonic source is constructed and arranged to operate most effectively substantially at the skin surface and a radius of treatment substantially less than 10 millimeters.

5. The device of claim 1, wherein the focused ultrasonic source comprises a substantially flat-faced ultrasonic source, and the device further comprises a focusing element acoustically coupled to said substantially flat-faced ultrasonic source to focus the energy from the ultrasonic source into a confined treatment region of tissue.

6. The device of claim 1, further comprising an output of said temperature sensor that provides a readable output indication of said temperature of said region of tissue being treated by the device.

7. The device of claim 1, further comprising an output of said temperature sensor that provides a readable output indication of a treatment elapsed time.

8. The device of claim 1, further comprising an output of said temperature sensor that provides a readable output indication of a treatment remaining time.

9. The device of claim 1, further comprising an output of said temperature sensor that provides a readable output indication of a treatment thermal dose.

10. The device of claim 1, further comprising an output of said temperature sensor that provides a readable output indication of an indication of treatment progress calculated from said sensed temperature.

11. The device of claim 1, further comprising a temperature control circuit that receives an input signal from said temperature sensor and provides a responsive output thereto that controls said acoustical energy of the device and as a result controls the temperature of said region of tissue being treated by the device.

12. The apparatus of claim 1, wherein the temperature sensor is disposed within a face of the ultrasonic source.

13. The apparatus of claim 1, wherein the temperature sensor is disposed within a coupling pad adapted to pass energy from said ultrasonic source to the region being treated and the coupling pad is electrically coupled to the apparatus to pass a signal from said temperature sensor to said control circuit within said apparatus.

14. The device of claim 1, further comprising a medicated patch having:
    an adhesive band adapted for adhering to a region of tissue being treated;
    said adhesive band including a first surface having an adhesive material for adhering to the skin around said region of tissue being treated;
    said adhesive band further including a second surface adapted for coupling to an ultrasonic source for treating said region of tissue;
    said patch being designed and adapted to pass ultrasonic waves from said ultrasonic source into said region of tissue; and
    said patch including medication known to aid the treatment of said skin condition.

15. The device of claim 14, wherein the patch is for the treatment of warts and wherein the medication includes salicylic acid.

16. The device of claim 14, further comprising a fluid coupling medium for aiding the transport of energy from the ultrasonic source into the region of tissue being treated.

17. The device of claim 16, wherein the fluid coupling medium itself includes a substance known to aid the treatment of said skin condition.

* * * * *